US007141051B2

(12) United States Patent
Janowski et al.

(10) Patent No.: US 7,141,051 B2
(45) Date of Patent: Nov. 28, 2006

(54) LOW PROFILE SPINAL FIXATION SYSTEM (75) Inventors: Brian P. Janowski, Marquette, MI (US); Francis J. Korhonen, Negaunee, MI (US); Thomas S. Kilpela, Marquette, MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 133 days.

(21) Appl. No.: 10/358,530

(22) Filed: Feb. 5, 2003

(65) Prior Publication Data
US 2004/0153068 A1 Aug. 5, 2004

(51) Int. Cl.
*A61B 17/58* (2006.01)
(52) U.S. Cl. .......................................... 606/61; 606/72
(58) Field of Classification Search .................. 606/61, 606/53, 60, 72, 73
See application file for complete search history.

(56) References Cited

U.S. PATENT DOCUMENTS

| 4,648,388 A | 3/1987 | Steffee |
| 4,653,481 A | 3/1987 | Howland et al. |
| 4,693,240 A | 9/1987 | Evans |
| 4,719,904 A | 1/1988 | Steffee |
| 4,763,644 A | 8/1988 | Webb |
| 4,771,767 A | 9/1988 | Steffee |
| 4,805,602 A | 2/1989 | Puno et al. |
| 4,854,311 A | 8/1989 | Steffee |
| 4,887,596 A | 12/1989 | Sherman |
| 4,913,134 A | 4/1990 | Luque |
| 4,930,732 A | 6/1990 | Hardtke |
| 4,946,458 A | 8/1990 | Harms et al. |
| 4,950,269 A | 8/1990 | Gaines, Jr. |
| 5,002,542 A | 3/1991 | Frigg |
| 5,005,562 A | 4/1991 | Cotrel |
| 5,024,213 A | 6/1991 | Asher et al. |
| 5,030,220 A | 7/1991 | Howland |
| 5,042,982 A | 8/1991 | Harms et al. |
| 5,053,034 A | 10/1991 | Olerud |
| 5,067,955 A | 11/1991 | Cotrel |
| 5,084,049 A | 1/1992 | Asher et al. |

(Continued)

FOREIGN PATENT DOCUMENTS

DE 3 625 542 C1 11/1987

(Continued)

OTHER PUBLICATIONS

Declaration of Richard V. Baratta, dated Jun. 1, 2005.

(Continued)

*Primary Examiner*—Eduardo C. Robert
*Assistant Examiner*—Jessica R. Baxter
(74) *Attorney, Agent, or Firm*—Fitch, Even, Tabin & Flannery (57) ABSTRACT A spinal fixation system is provided that, in one form, includes a coupling member having a cam lock member that is fixed against translation as it is turned with turning of the cam lock member causing an elongate member such as a spinal rod to be pushed downward in the coupling member for fixing the rod therein. In another aspect, the rod is fixed against a low profile insert that seats in a recess formed in the head of an anchor member projecting from the coupling member. The insert has an upper surface against which the rod is fixed. In one form, the insert upper surface is flat to provide for line contact against the rod so as to minimize damage thereto. In another form, the cam lock member cams against a clamping member driving it downward in the coupling member for fixing the rod therein.

21 Claims, 9 Drawing Sheets

U.S. PATENT DOCUMENTS

| | | |
|---|---|---|
| 5,092,867 A | 3/1992 | Harms et al. |
| 5,129,388 A | 7/1992 | Vignaud et al. |
| 5,129,899 A | 7/1992 | Small et al. |
| 5,129,900 A | 7/1992 | Asher et al. |
| 5,154,719 A | 10/1992 | Cotrel |
| 5,176,680 A | 1/1993 | Vignaud et al. |
| 5,190,543 A | 3/1993 | Schlapfer |
| 5,196,013 A | 3/1993 | Harms et al. |
| 5,207,678 A | 5/1993 | Harms et al. |
| 5,209,751 A | 5/1993 | Farris et al. |
| 5,217,497 A | 6/1993 | Mehdian |
| 5,257,993 A | 11/1993 | Asher et al. |
| 5,261,907 A | 11/1993 | Vignaud et al. |
| 5,261,910 A | 11/1993 | Warden et al. |
| 5,261,912 A | 11/1993 | Frigg |
| 5,261,913 A | 11/1993 | Marnay |
| 5,275,601 A | 1/1994 | Gogolewski et al. |
| 5,306,275 A | 4/1994 | Bryan |
| 5,312,404 A | 5/1994 | Asher et al. |
| 5,330,473 A | 7/1994 | Howland |
| 5,334,203 A | 8/1994 | Wagner |
| 5,344,422 A | 9/1994 | Frigg |
| 5,346,493 A | 9/1994 | Stahurski et al. |
| 5,360,431 A | 11/1994 | Puno et al. |
| 5,369,594 A | 11/1994 | Huang et al. |
| 5,385,583 A | 1/1995 | Cotrel |
| 5,429,639 A | 7/1995 | Judet |
| 5,437,669 A | 8/1995 | Yuan et al. |
| 5,437,670 A | 8/1995 | Sherman et al. |
| 5,443,467 A | 8/1995 | Biedermann et al. |
| 5,466,237 A | 11/1995 | Byrd, III et al. |
| 5,474,551 A | 12/1995 | Finn et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,489,307 A | 2/1996 | Kuslich et al. |
| 5,496,321 A | 3/1996 | Puno et al. |
| 5,498,263 A | 3/1996 | DiNello et al. |
| 5,498,264 A | 3/1996 | Schlapfer et al. |
| 5,520,689 A | 5/1996 | Schlapfer et al. |
| 5,522,816 A | 6/1996 | Dinello et al. |
| 5,536,268 A | 7/1996 | Griss |
| 5,545,167 A | 8/1996 | Lin |
| 5,549,608 A | 8/1996 | Errico et al. |
| 5,554,157 A | 9/1996 | Errico et al. |
| 5,562,663 A | 10/1996 | Wisnewski et al. |
| 5,584,831 A | 12/1996 | McKay |
| 5,591,165 A | 1/1997 | Jackson |
| 5,593,407 A | 1/1997 | Reis |
| 5,613,967 A | 3/1997 | Engelhardt et al. |
| 5,615,965 A | 4/1997 | Saurat et al. |
| 5,624,442 A | 4/1997 | Mellinger et al. |
| 5,628,740 A | 5/1997 | Mullane |
| 5,630,817 A | 5/1997 | Rokegem et al. |
| 5,667,508 A | 9/1997 | Errico et al. |
| 5,669,911 A | 9/1997 | Errico et al. |
| 5,672,176 A | 9/1997 | Biedermann et al. |
| 5,683,390 A | 11/1997 | Metz-Stavenhagen et al. |
| 5,683,392 A | 11/1997 | Richelsoph et al. |
| 5,690,629 A | 11/1997 | Asher et al. |
| 5,690,630 A | 11/1997 | Errico et al. |
| 5,702,393 A | 12/1997 | Pfaifer |
| 5,702,395 A | 12/1997 | Hopf |
| 5,716,355 A | 2/1998 | Jackson et al. |
| 5,716,358 A | 2/1998 | Ochoa et al. |
| 5,728,098 A | 3/1998 | Sherman et al. |
| 5,733,286 A | 3/1998 | Errico et al. |
| 5,741,254 A | 4/1998 | Henry et al. |
| 5,741,255 A | 4/1998 | Krag et al. |
| 5,743,907 A | 4/1998 | Asher et al. |
| 5,752,957 A | 5/1998 | Ralph et al. |
| 5,776,134 A | 7/1998 | Howland |
| 5,782,833 A | 7/1998 | Haider |
| 5,797,911 A | 8/1998 | Sherman et al. |
| 5,810,819 A | 9/1998 | Errico et al. |
| 5,817,094 A | 10/1998 | Errico et al. |
| 5,879,350 A | 3/1999 | Sherman et al. |
| 5,888,221 A | 3/1999 | Gelbard |
| 5,891,145 A | 4/1999 | Morrison et al. |
| 5,899,902 A | 5/1999 | Brown et al. |
| 5,910,142 A | 6/1999 | Tatar |
| 5,928,233 A | 7/1999 | Apfelbaum |
| 5,961,517 A | 10/1999 | Biedermann et al. |
| 5,964,767 A | 10/1999 | Tapia et al. |
| 5,984,922 A | 11/1999 | McKay |
| 5,989,250 A | 11/1999 | Wagner et al. |
| 5,989,254 A | 11/1999 | Katz |
| 5,997,539 A | 12/1999 | Errico et al. |
| 6,004,349 A | 12/1999 | Jackson |
| 6,010,503 A | 1/2000 | Richelsoph et al. |
| 6,015,409 A | 1/2000 | Jackson |
| 6,039,738 A | 3/2000 | Sanders et al. |
| 6,050,997 A | 4/2000 | Mullane |
| 6,074,391 A | 6/2000 | Metz-Stavenhagen et al. |
| 6,077,262 A | 6/2000 | Schlapfer et al. |
| 6,080,156 A | 6/2000 | Asher et al. |
| 6,083,226 A | 7/2000 | Fiz |
| 6,086,588 A | 7/2000 | Ameil et al. |
| 6,090,111 A | 7/2000 | Nichols |
| 6,110,172 A | 8/2000 | Jackson |
| 6,113,601 A | 9/2000 | Tatar |
| 6,123,706 A | 9/2000 | Lange |
| 6,146,383 A | 11/2000 | Studer et al. |
| 6,179,838 B1 | 1/2001 | Fiz |
| 6,179,841 B1 | 1/2001 | Jackson |
| 6,183,478 B1 | 2/2001 | Konieczynski |
| 6,187,005 B1 | 2/2001 | Brace et al. |
| 6,235,033 B1 | 5/2001 | Brace et al. |
| 6,258,090 B1 | 7/2001 | Jackson |
| 6,280,442 B1 | 8/2001 | Barker et al. |
| 6,302,888 B1 | 10/2001 | Mellinger et al. |
| 6,309,389 B1 | 10/2001 | Baccelli |
| 6,371,957 B1 | 4/2002 | Amrein et al. |
| 6,379,356 B1 | 4/2002 | Jackson |
| 6,478,797 B1 | 11/2002 | Paul |
| 6,485,491 B1 | 11/2002 | Farris et al. |
| 6,485,494 B1 | 11/2002 | Haider |
| 6,488,681 B1 | 12/2002 | Martin et al. |
| 6,488,682 B1 | 12/2002 | Kikuchi et al. |
| 6,524,315 B1 | 2/2003 | Selvitelli et al. |
| 6,540,748 B1 | 4/2003 | Lombardo |
| 6,554,834 B1 | 4/2003 | Crozet et al. |
| 6,565,565 B1 | 5/2003 | Yuan et al. |
| 6,592,585 B1 | 7/2003 | Choi et al. |
| 6,755,829 B1 * | 6/2004 | Bono et al. .................. 606/61 |
| 2001/0001119 A1 | 5/2001 | Lombardo |
| 2001/0012937 A1 | 8/2001 | Schaffler-Wachter et al. |
| 2001/0029374 A1 | 10/2001 | Kikuchi et al. |
| 2002/0010467 A1 | 1/2002 | Cooper et al. |
| 2002/0026193 A1 | 2/2002 | Barker et al. |
| 2002/0049446 A1 | 4/2002 | Harkey, III et al. |
| 2002/0052603 A1 | 5/2002 | Nichols et al. |
| 2002/0082602 A1 | 6/2002 | Biedermann et al. |
| 2002/0091386 A1 | 7/2002 | Martin et al. |
| 2002/0111626 A1 | 8/2002 | Ralph et al. |
| 2002/0111628 A1 | 8/2002 | Ralph et al. |
| 2002/0116001 A1 | 8/2002 | Schafer et al. |
| 2002/0120272 A1 | 8/2002 | Yuan et al. |
| 2002/0133154 A1 | 9/2002 | Saint Martin |
| 2002/0143330 A1 | 10/2002 | Shluzas |
| 2002/0151900 A1 | 10/2002 | Glascott |
| 2002/0161370 A1 | 10/2002 | Frigg et al. |
| 2002/0183748 A1 | 12/2002 | Martin et al. |
| 2003/0004511 A1 | 1/2003 | Ferree |

| | | | |
|---|---|---|---|
| 2003/0023240 A1 | 1/2003 | Amrein et al. | |
| 2003/0036758 A1 | 2/2003 | Frigg et al. | |
| 2003/0125742 A1 | 7/2003 | Yuan et al. | |

FOREIGN PATENT DOCUMENTS

| | | |
|---|---|---|
| DE | 37 11 013 C1 | 6/1988 |
| DE | 38 02 833 A1 | 9/1988 |
| DE | 39 16 198 A1 | 11/1990 |
| DE | 9 403 231 | 6/1994 |
| EP | 0 242 708 A2 | 10/1987 |
| EP | 0 284 559 A1 | 9/1988 |
| EP | 0 303 773 | 2/1989 |
| EP | 0 318 356 A1 | 5/1989 |
| EP | 0 348 272 A1 | 12/1989 |
| EP | 0 348 272 B1 | 12/1989 |
| EP | 0 384 001 A1 | 8/1990 |
| EP | 0 441 729 A1 | 8/1991 |
| EP | 0 446 092 A1 | 9/1991 |
| EP | 0 452 792 A1 | 10/1991 |
| EP | 0 558 883 A1 | 9/1993 |
| EP | 0 870 474 A1 | 10/1998 |
| EP | 1 090 595 A2 | 10/1999 |
| EP | 1 138 267 A2 | 10/2001 |
| EP | 1 174 092 A2 | 1/2002 |
| EP | 1 190 678 A2 | 3/2002 |
| EP | 1 210 914 A1 | 6/2002 |
| EP | 1 222 899 A2 | 7/2002 |
| EP | 1 234 547 A1 | 8/2002 |
| FR | 2 642 642 | 8/1990 |
| FR | 2 682 280 | 4/1993 |
| FR | 2 683 445 | 5/1993 |
| FR | 2 778 087 | 11/1999 |
| FR | 2 810 533 | 12/2001 |
| GB | 2 157 179 A | 10/1985 |
| GB | 2 365 345 A | 2/2002 |
| JP | 2 198549 | 8/1990 |
| WO | WO 91/01115 | 2/1991 |
| WO | WO 91/01691 | 2/1991 |
| WO | WO 91/16020 | 10/1991 |
| WO | WO 93/07823 | 4/1993 |
| WO | WO 93/11715 | 6/1993 |
| WO | WO 94/08527 | 4/1994 |
| WO | WO 94/10927 | 5/1994 |
| WO | WO 94/10944 | 5/1994 |
| WO | WO 94/14384 | 7/1994 |
| WO | WO 94/26191 | 11/1994 |
| WO | WO 99/56652 | 11/1999 |
| WO | WO 99/65415 | 12/1999 |
| WO | WO 01/03593 A1 | 1/2001 |
| WO | WO 02/30307 A2 | 4/2002 |
| WO | WO 02/054966 A2 | 7/2002 |
| WO | WO 02/094114 A1 | 11/2002 |
| WO | WO 03/024343 A1 | 3/2003 |

OTHER PUBLICATIONS

Pioneer's Opposition to Defendants' Motion for Summary Judgement that the '565 Patent is not Invalid, dated Jun. 1, 2005.

Pioneer's Opposition to Defendants' Motion for Summary Judgement of Infringement, dated Jun. 1, 2005.

Order dated Oct. 13, 2005, Case No. 2:05-CV-41, Western District of Michigan Northern Division.

Opinion dated Oct. 13, 2005, Case No. 2:05-CV-41, Western District of Michigan Northern Division.

* cited by examiner

LOW PROFILE SPINAL FIXATION SYSTEM

FIELD OF THE INVENTION

The invention relates to spinal fixation systems and, more particularly, to spinal fixation systems that have a low profile.

BACKGROUND OF THE INVENTION

Spinal rods for immobilizing vertebral bones of the spinal column are typically anchored to the vertebrae via bone screws that extend through the pedicle into the vertebral bodies or by hooks that engage about the vertebrae. The rods are connected to the anchor members by generally yoke-shaped couplers that can be either integral with the anchor member head or separate components from the anchor member for use in polyaxial pedicle screw systems for spinal rod fixation. These prior systems employ some sort of compression member that is brought down into engagement either directly or indirectly with the spinal rod for securing it relative to the anchor member, and in polyaxial systems for securing the anchor member relative to the coupler.

For this purpose, the compression member and coupler typically are engaged via threading therebetween such that the compression member is threaded down into its locked position in or about the yoke-shaped coupler. Alternatively, wedge cam surfaces between radial flanges on the compression member and radial recesses in the coupler walls have also been employed to advance the compression member for pushing the spinal rod down into fixed position relative to the screw anchor member, see U.S. Patent Application Publication No. US 2002/0120272 to Yuan et al. The problem with the threaded or cam wedge systems of spinal rod locking is that to allow the compression member to advance relative to the coupler, the size or profile of the coupler as well as the compression member necessarily is increased. In other words, to have threads or cam surfaces formed on the coupler requires that the walls be provided with a sufficient axial extent for the advancement of the threaded or cammed compression member therealong.

In polyaxial spinal fixation systems, the use of inserts between the head of the anchor member and the spinal rod has been proposed, see U.S. Pat. No. 5,733,286 to Errico et al. The large hemispherical insert of Errico et al. is engaged on a concave recess formed in a screw head received in the coupler allowing the coupler to adjust relative to the polyaxial pedicle screw for receipt of the spinal rod in its desired position. However, the entire Errico et al. system has a undesirably large profile as it employs a threaded set screw for clamping on the spinal rod, and the hemispherical insert extends well beyond the top of the screw head into the coupler channel through which the spinal rod is received.

SUMMARY OF THE INVENTION

In accordance with the present invention, a low-profile spinal fixation system is provided. In one aspect, a cam lock member of a coupling device is fixed against translation as it is turned so that a cam surface of the lock member causes an elongate member that extends generally along the spinal column, e.g. spinal rod, to be forced or pushed downward. As the cam lock member does not translate along the coupling device, the size of the coupling device can be kept to a minimum. Further, the low profile of the present system may allow for minimally invasive surgical procedures to be employed therewith such as with the components thereof being cannulated for use with a guide wire.

In another aspect, a polyaxial spinal fixation system is provided having a coupling member including an internal seat surface and a central bore sized to allow the anchor member to extend through the bore in several different orientations. The anchor member includes a head having an upper recess in which a low profile insert is provided. The insert has an upper surface that may be substantially flat, may have radially oriented concave paths or valleys so that the insert rotates to the closest path to meet with the spinal rod, or may have a cup or peripheral ridge that deforms when compressed by the spinal rod to form a path without deforming the spinal rod. The upper surface is fit in the head recess with the insert sized so that the upper surface projects only slightly beyond the proximal end of the anchor member to keep the profile of the insert to a minimum.

In a preferred form, the insert has an enlarged lower portion having a lower arcuate surface thereon for bearing against the concave recess surface of the anchor member head, and a central projection that extends upwardly from the lower portion and includes the flat upper surface thereon. The anchor member head preferably includes a retainer such as in the form of staked portions that allow the insert to self-adjust as the angle of the coupling member is adjusted with the flat surface projecting above the anchor member head for engaging the spinal rod.

DETAILED DESCRIPTION OF THE PREFERRED EMBODIMENTS

Figure 1:
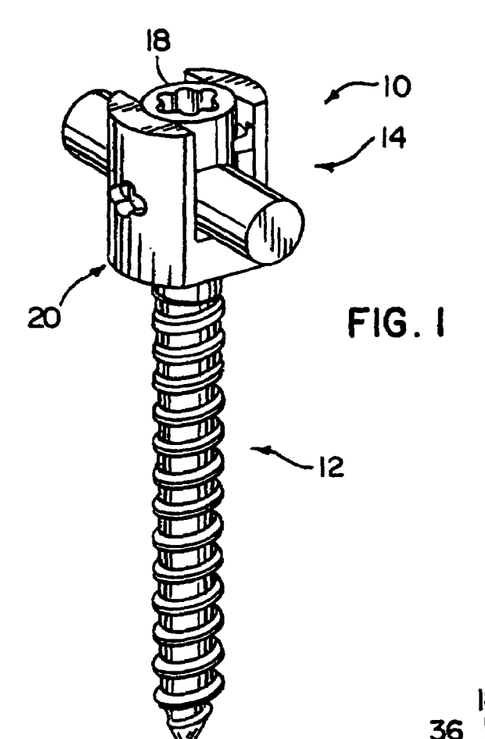
FIG. 1 is a perspective view of the spinal fixation system in accordance with the present invention showing a bone screw and a coupling device including a coupling member and a cam lock member for securing a spinal rod relative to the bone screw.
Figure 2:
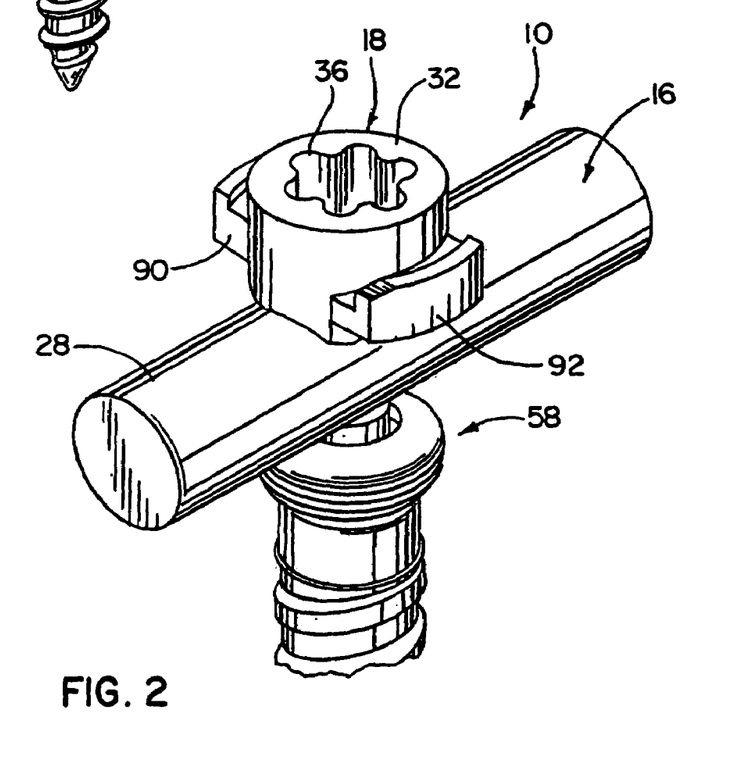
FIG. 2 is an enlarged perspective view of the spinal fixation system of FIG. 1 with the coupling member removed to better illustrate the cam lock member and to show the configuration of the head of the bone screw.
Figures 3, 4:
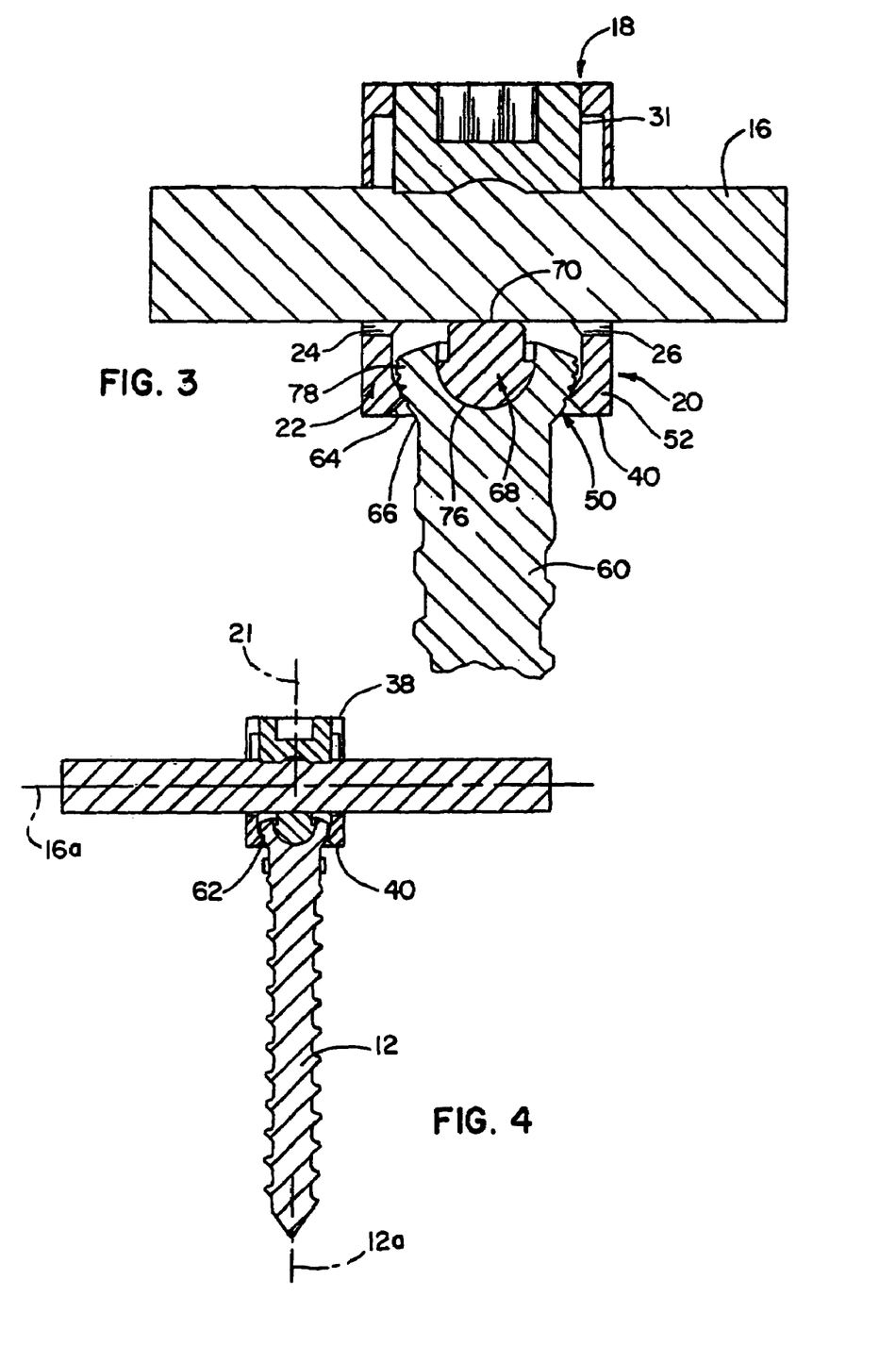
FIG. 3 is a cross-sectional view of the spinal fixation system showing a recess formed in the screw head in which a low profile anvil insert is received for clamping of the spinal rod thereagainst.
FIG. 4 is a cross-sectional view similar to FIG. 3 showing the relative sizes of the various components of the spinal fixation system.

In FIGS. 1 and 2, a low profile spinal fixation system 10 in accordance with the present invention is depicted. As shown, the spinal fixation system 10 includes a bone anchor member in the form of a bone screw 12 and a coupling device generally designated 14. The coupling device 14 is operable to secure an elongate member in the form of spinal rod 16 in place relative to the bone screw 12. The coupling device 14 includes a compression or cam lock member 18 and a coupling member 20, which cooperate to secure the spinal rod 16 relative to the bone screw 12 anchored in a vertebral bone with the rod 16 generally extending axially along the spinal column. The coupling device 14 and specifically the cam lock member 18 and coupling member 20 are provided with a compact configuration. In particular, the cam lock member 18 and coupling member 20 are provided with a very low profile in a direction indicated by axis line 21 extending transverse and specifically orthogonally to the axis 16a of the spinal rod 16 fixed relative to the bone screw 12 by the coupling device 14, as best seen in FIG. 4.

More specifically, the low profile of the coupling device 14 is obtained by having the cam lock member 18 be effective to lock the spinal rod 16 without the need to advance the cam lock member 18 along the coupling member 20. In this regard, the coupling member 20 can be provided with a body 22 having side openings 24 and 26 through which the spinal rod 16 passes with the body 22 free of any threading or cam surfaces that cooperate with the cam lock member 18 for locking of the spinal rod 16 relative to the bone screw 12. Instead, the cam lock member 18 is fixed against translation relative to the coupling member 20, and preferably cooperates with the outer curved surface 28 of the rod 16 itself to secure it in position relative to the screw 12.

Figure 8:
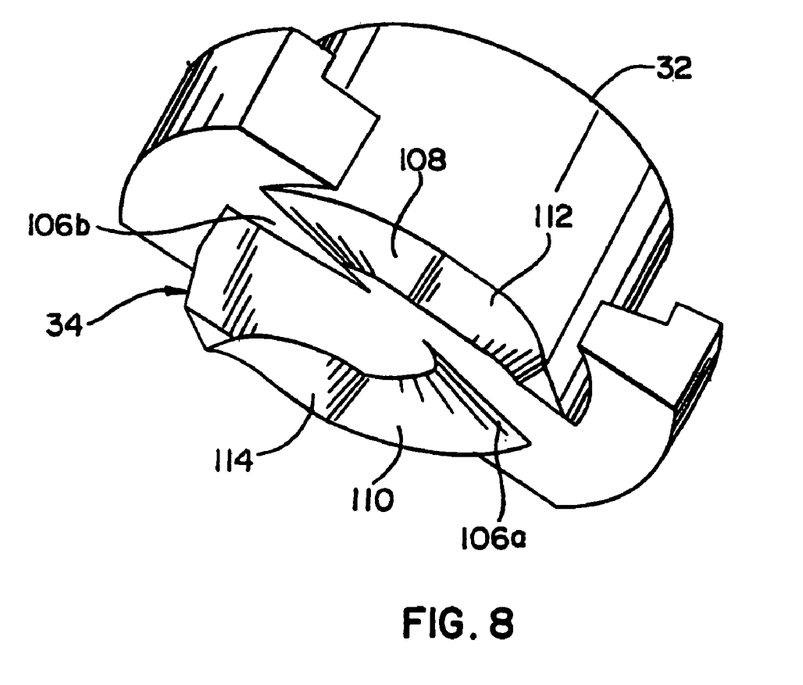
Figure 9:
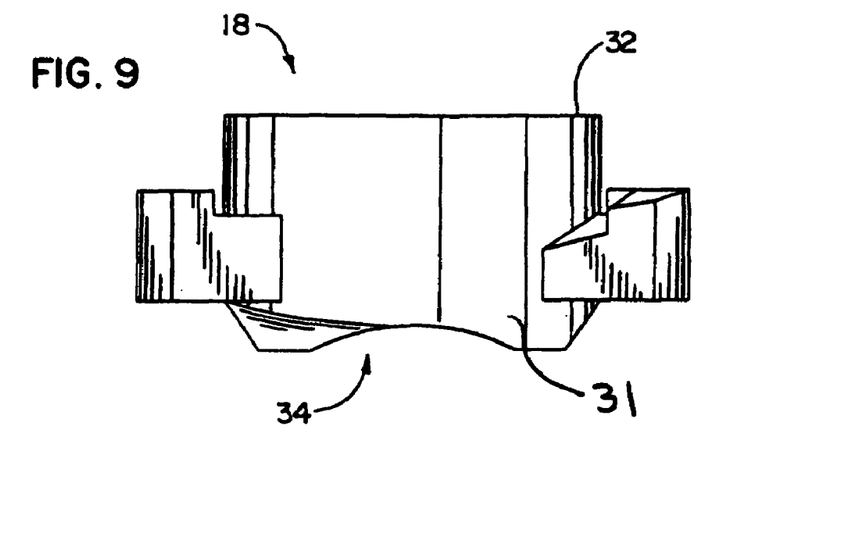
Figure 10:
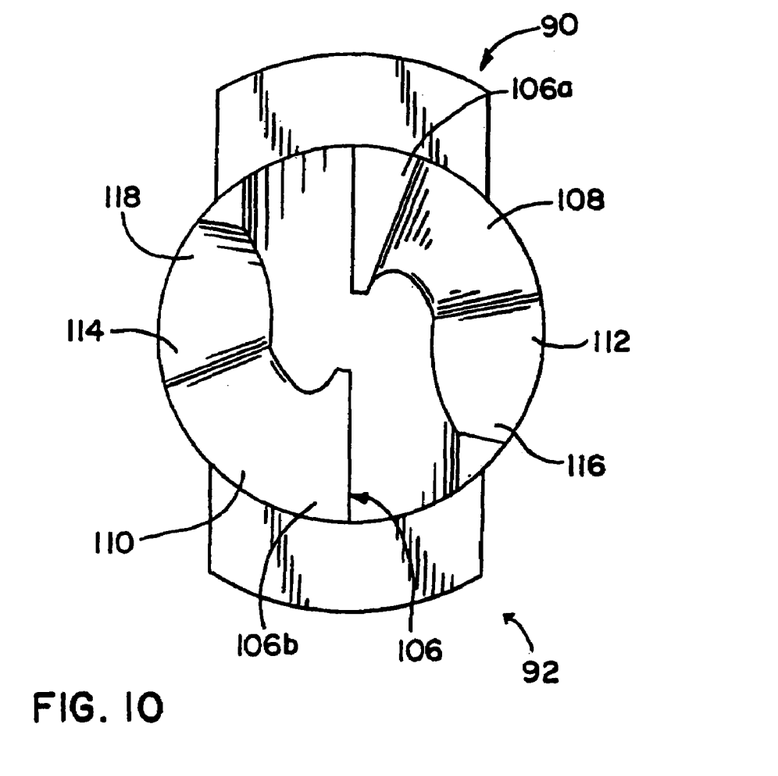

For this purpose, the cam lock member 18 has a generally annularly configured body 30 having a very short axial extent along turning axis 21 thereof via annular side surface 31 extending between its top and bottom surfaces 32 and 34. The top surface 32 is provided with driving surface portions 36 which cooperate to form a predetermined configuration for the receipt of a similarly configured drive tool for turning the cap member 18 between unlocked and locked positions thereof. The bottom surface 34 is programmed or contoured to provide a camming action on the curved surface 28 of the rod 16 when the cam lock member 18 is turned, as best seen in FIGS. 8 and 10 and as will be described more fully hereinafter.

Figure 16:
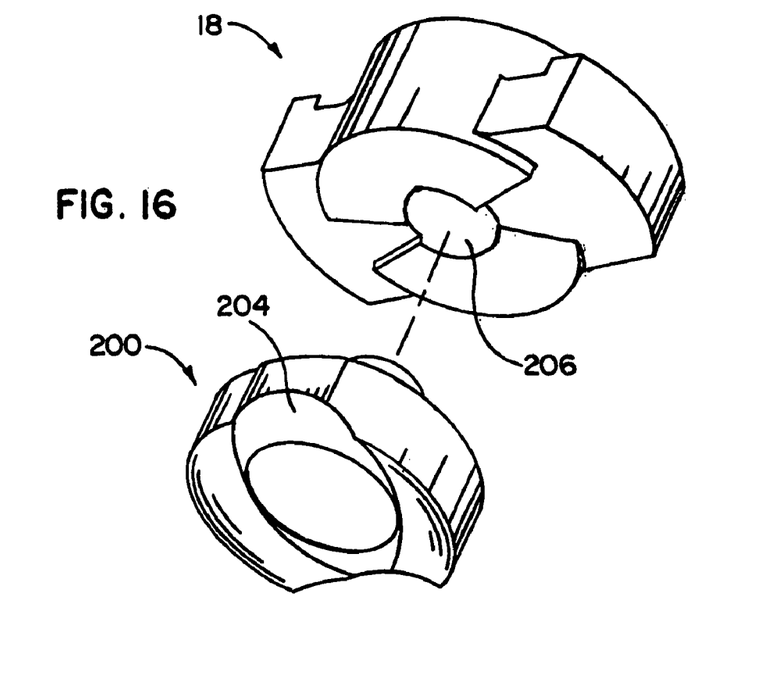
FIGS. 16–18 are various views of alternative camming system employing both a cam lock member and a saddle member.
Figure 17:
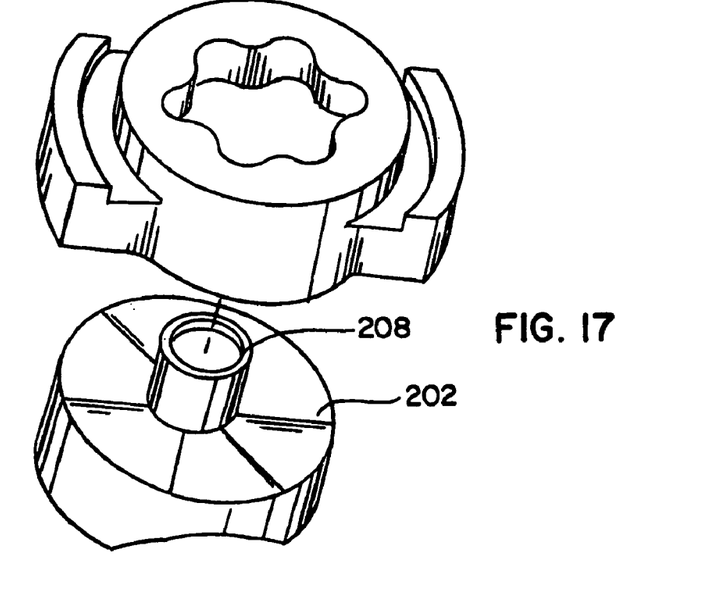
Figure 18:
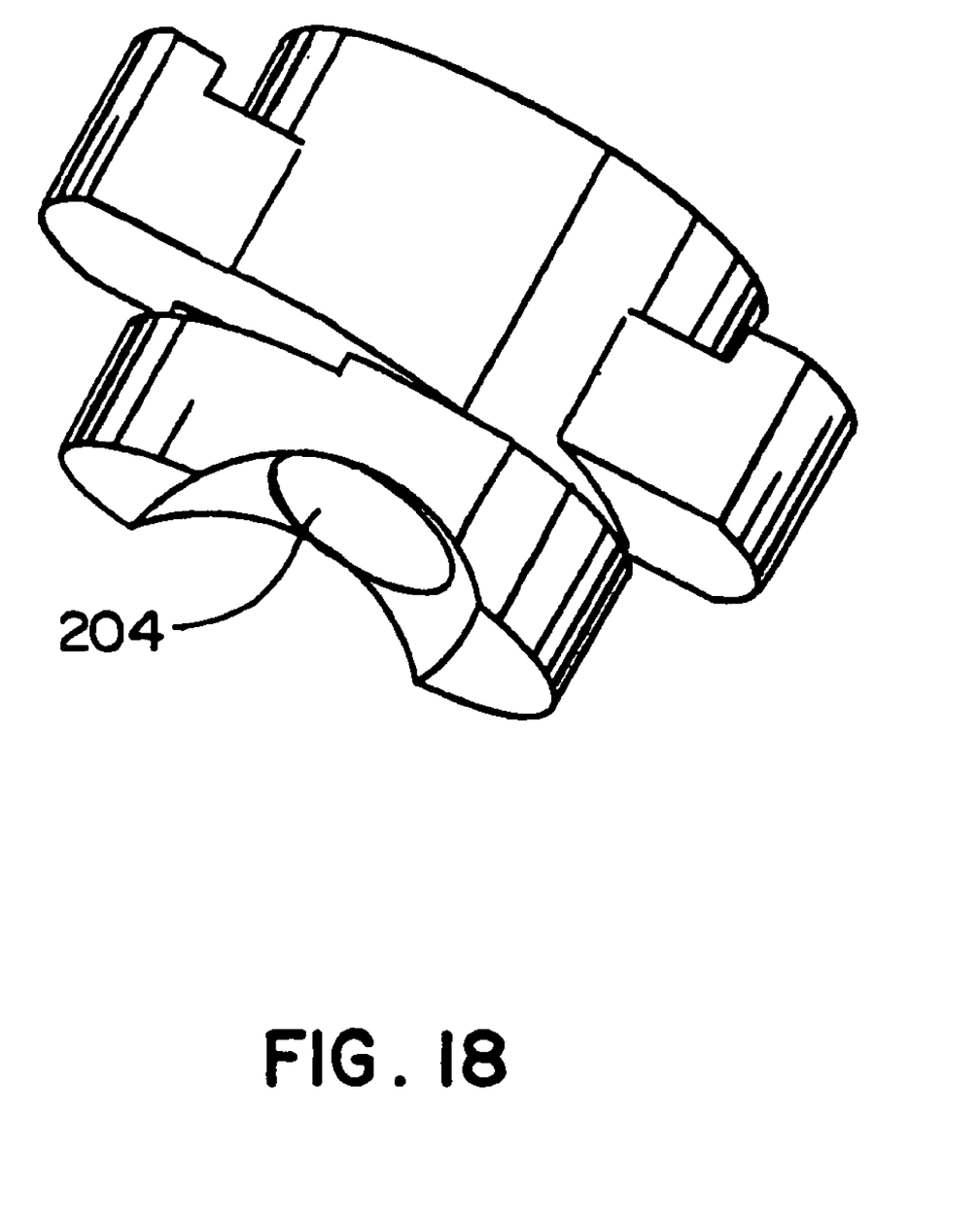

Although less preferred in terms of maintaining a low profile for the spinal fixation system 10 herein, an intermediate saddle member 200 can be provided between the lock member 18 and spinal rod 16, as shown in FIGS. 16–18. The saddle member 200 has an upper cam surface 202 configured for cooperation with lock member cam surface 34 when the lock member 18 is turned to its locked position so that the saddle member 200 shifts downwardly along axis 21 for clamping against the rod 16. The saddle member is provided with a curved bottom surface 204 which substantially matches the curvature of rod surface 28 so that the saddle member 200 engages and pushes against the rod 16 without camming thereagainst. The cam lock member 18 can include a center opening 206 which receives a central post 208 projecting upward from the saddle member 200 to keep the cam lock member 18 and saddle member 200 oriented properly with respect to each other.

Figure 11:
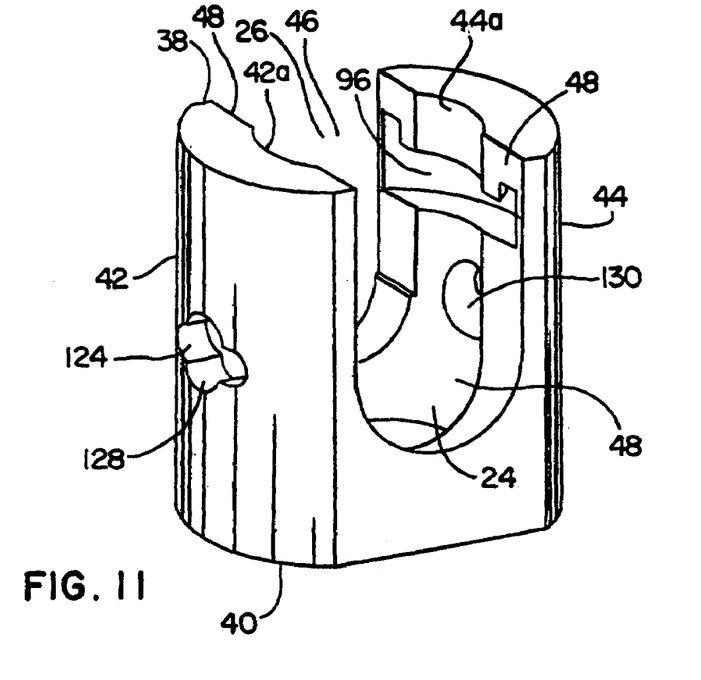
FIGS. 11–13 are various views of the yoke-shaped coupling member.
Figure 12:
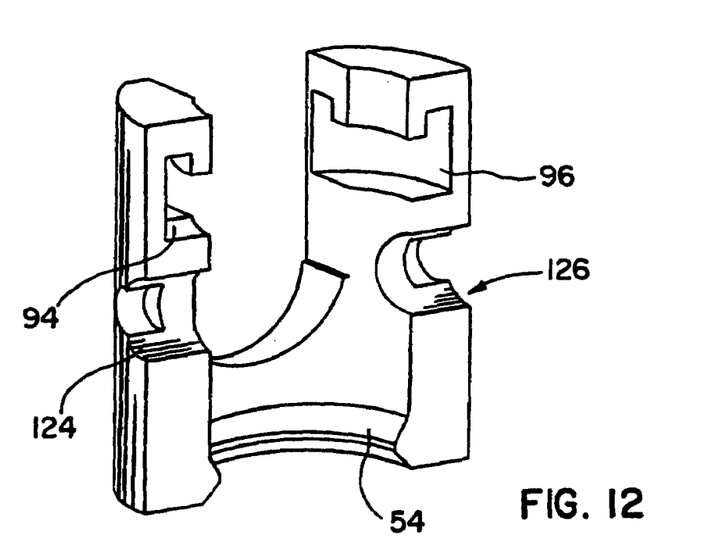
Figure 13:
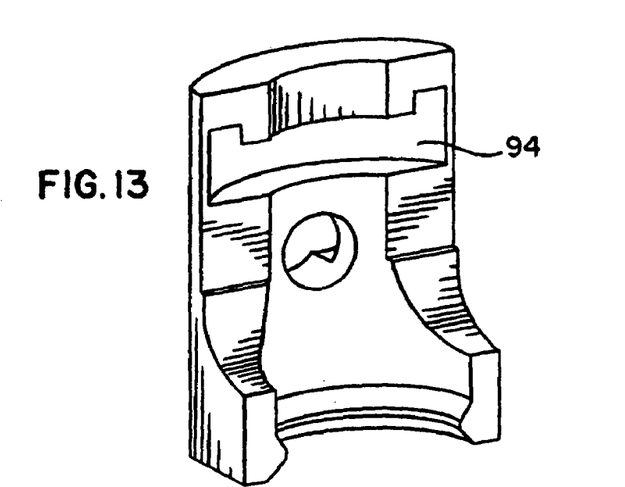
Figure 14:
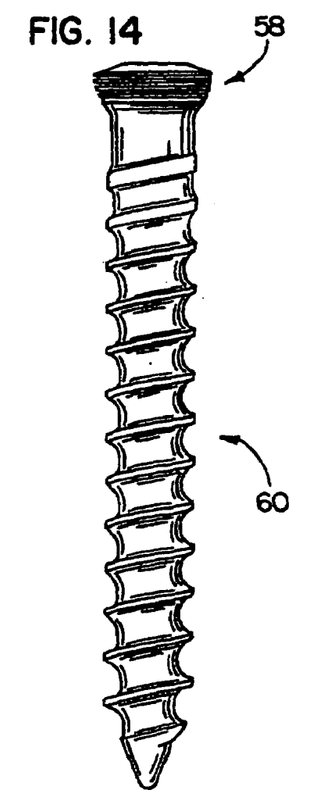
FIGS. 14 and 15 are elevational and sectional views, respectively, of the bone screw anchor member.

Similar to the cam lock member 18, the coupling member 20 also has a relatively small axial extent between top and bottom surfaces 38 and 40 thereof. As best seen in FIG. 11, the body 22 of the coupling member generally has a U-shaped or yoke configuration including opposing upstanding walls 42 and 44 spaced from each other by the rod openings 24 and 26 which can have an elongate configuration and be open to the top 38 of the coupling member body 22. Since the cam lock member 18 need not be advanced down along the walls 42 and 44 in the direction 21, the size in this direction can be minimized. By way of example and not limitation, the length or distance that the walls 42 and 44 extend between the top 38 and bottom 40 of the coupling member body 22 can be approximately 13.47 millimeters. The cam lock member 18 has a profile along axis 21 between the top 32 and the lowest most point of the contoured bottom cam surface 34 of approximately 5.08 mm.

Figure 5:
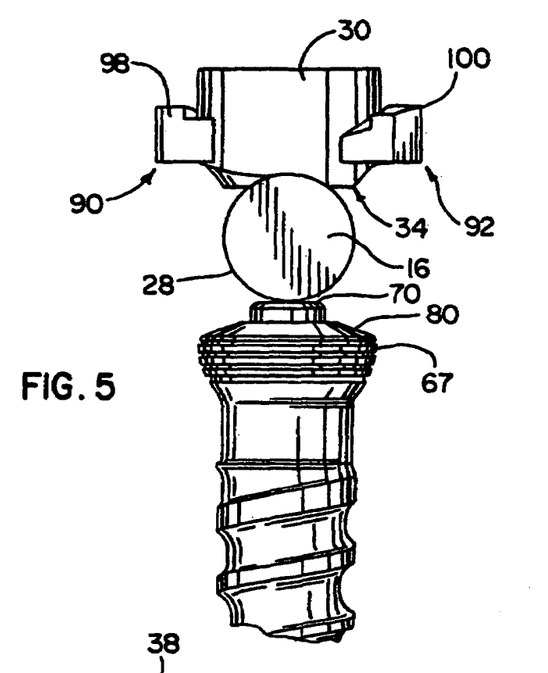
FIG. 5 is a elevational view similar to FIG. 2 with the coupling member removed to show the radial flanges on the cam lock member and a bottom cam surface thereof.

As shown, the annular body 30 of cam lock member 18 is sized to fit in internal space 46 of the coupling member 20 between the arcuate walls 42 and 44 thereof. The walls 42 and 44 are free of threading or cam surfaces that cooperate with the cam lock member 18 for shifting it to a locked position. More particularly, the inner surface 48 of the coupling member 20 including arcuate surface portions 42a and 44a on the respective coupling member walls 42 and 44 are sized to closely receive the outer surface 31 of the cam lock member annular body 30 therebetween. These surface portions 42a and 44a are each free of threading or cam surfaces and thus only serve as guide surfaces for the cam lock member body 30 as it is turned about axis 21. Since the walls 42 and 44 do not need to be threaded or provided with recessed cam surfaces or the like, the size of the coupling device 14 can be kept to a minimum in the widthwise direction along the axis 16a of the spinal rod 16 as well. By way of example and not limitation, the diametrical width of the coupling device along spinal rod axis 16a can be approximately 10.03 millimeters. As can be seen in FIG. 5, guides 45 may be provided. The guides 45 are provided to initially pilot the cam lock member 18 into engagement with the walls 42 and 44.

Referring next to FIGS. 3 and 4, the illustrated spinal fixation system 10 has a polyaxial bone screw 12 whose orientation can be changed such that its longitudinal axis 12a extends transverse to the axis 21 of the coupling device 14 or is substantially aligned therewith. To this end, the coupling device 18, and specifically the coupling member 20 thereof is provided with a bottom throughbore 50 that extends through bottom wall 52 of the coupling member 20. The bottom wall 52 includes an inner surface portion 54 that tapers or curves inwardly from the surface portions 42a and 44a toward the center axis 21. The diameter across the inner surface portion 54 at its lowermost end 56 is sized to be smaller than an enlarged head 58 of the bone anchor screw 12. In addition, the diameter at 56 is sufficiently large to allow the threaded shank 60 depending from the screw head 58 to be advanced therethrough. In this manner, the inner surface portion 54 serves as a seating surface for the screw head 58. As an alternative, the diameter 56 is threaded with a thread oversized relative to the shank 60, thereby allowing the screw shank 60 to be loosely threaded through. In this instance, the diameter 56 is sized as to hold the shank 60 from passing easily through so that the screw 12 and coupling member 20 may be handled by a surgeon as a single component during the operation. In addition, the oversized threads allow the screw to be polyaxial in its orientation. As a further alternative, the screw 12 may be passed through the diameter 56, and a c-ring or radial spring may be attached to the screw 12 immediately adjacent to the coupling member 20, thereby holding the two together and allowing the surgeon to utilize them as a single component during the operation.

The throughbore 50 extends centrally through the inner surface portion 54 and includes an enlarged diameter lower portion 62 formed by tapered or curved surface portion 64 on the bottom wall 52 of the coupling member 20. The tapered surface portion 64 extends from the smallest diameter of the bore 50 at 56 tapering outwardly relative to the center axis 21 of the coupling member 20 to the bottom surface 30 thereof. The enlarged bore portion 62 allows the screw 12 to swivel or pivot to a variety of different orientations thereof relative to the coupling device 14. For example, in the illustrated form, the enlarged bore portion 62 allows the screw shank to pivot by 20 degrees on either side of the coupling device axis 21. As the screw 12 is pivoted, the outer arcuate surface 66 of the screw head 58 rides or shifts on the tapered seat surface 54 in the coupling member 20. Once the orientation of the coupling device 14 relative to the bone screw 12 fastened into a vertebral bone is determined with the spinal rod 16 extending through the coupling member 20 and up along the spinal column, the cam lock member 18 is then turned to its locked position. In the locked position, the cam lock member 18 anchors the rod 16 to the spinal column so it is fixed relative to the bone screw 12 fastened into a vertebral bone with the bone screw head 58 clamped against the seat 54 therefor in the coupling member 20 thereby fixing coupling device 14 against shifting relative to the bone screw 12. The outer screw head surface 66 can be configured with concentric friction enhancing ridges or helical threads 67 to enhance the locking action between the screw head 58 and the seat 54.

Continuing reference to FIGS. 3 and 4, it can be seen that in the preferred and illustrated polyaxial spinal fixation system 10, the spinal rod 16 is pushed downwardly for being clamped against a small anvil insert 68. It should be noted that the previously described low profile coupling device 14 could be employed in spinal fixation systems that are not polyaxial and/or which do not employ an insert as described hereinafter. Similarly, the present insert 68 could be advantageously employed in systems that employ threads or cams in the coupling members thereof.

The insert 68 has an upper anvil surface 70 that engages against the underside of the spinal rod surface 28 to maintain enhanced contact therewith over the curved surfaces of bone screw heads used in prior systems. The insert 68 has an upper surface 70 that may be substantially flat, may have radially oriented concave paths or valleys so that the insert 68 rotates to the closest path to meet with the spinal rod surface 28, or may have a cup or peripheral ridge that deforms when compressed by the spinal rod 12 to form a path without deforming the spinal rod. Accordingly, the insert 68 provides at least a line of contact with the curved rod surface 28, whereas prior systems engaging spinal rods with their curved fastener heads have a point contact with the spinal rod when clamped thereagainst which can more easily damage the rod 16.

The present insert 68 is also provided with a very low profile to minimize the space it takes up in the coupling member 20. More particularly, the bone screw anchor 12 as an upper concave recess 72 formed in the screw head 58 thereof to form a cup-shaped wall 73 of the screw head 58 having an upwardly opening cavity 74 in which insert 68 is received. The insert 68 has an arcuate bottom surface 76 having a curvature similar to that of the concave surface 72 so that it can shift or slide thereon as the polyaxial screw 12 is moved to various orientations thereof relative to the coupling device 14. The insert 68 is sized such that the distance between the lower most point of the bottom surface 76 and the top flat surface 70 is slightly larger than the depth of the cavity 74. In this manner, the flat surface 70 projects only slightly above the proximal end 78 of the screw 12 at the top surface 80 of the screw head wall 73 extending about the cavity 74, as can be best seen in FIG. 5. Accordingly, the insert 68 only nominally increases the height of the screw head 58 in the internal space 46 of the coupling member 20 allowing the coupling device 14 to maintain its low profile character, as previously described. By way of example, the distance between the bottom 40 of the coupling member 20 and the spinal rod axis 16a with the rod 16 clamped against the insert 68 can be approximately 6.34 millimeters. It is preferred that the insert 68 has a greater elastic deformation than the coupling member 20 or the spinal rod 16 so that it has a greater spring-like property. Accordingly, the material of the insert 68 preferably has a lower Young's Modulus than the coupling member 20 and spinal rod, thereby reducing the criticality of the dimensional tolerances.

In the preferred and illustrated form, the small, low profile insert 68 has an enlarged lower portion 82 including the arcuate bottom surface 76 thereon with an upper portion 84 projecting centrally upward from the enlarged lower portion 82 and having the top surface 70 thereon. Accordingly, the top surface 70 is narrower in the directions orthogonal to the axis 21 then the bottom surface 76 so that a shoulder surface 86 is formed between the insert portions 82 and 84. The above-described structure for the low profile insert 68 provides it with an inverted mushroom-like configuration with the enlarged head portion 82 riding on the concave recess surface 72 in the screw head 58.

To keep the insert 68 in the cavity 74 formed in the screw head 58, a retainer such as in the form of staked portions 86 of the screw head wall 73 are provided. These staked portions 86 extend radially inward at the proximal end 78 of the screw 12 so as to be in interference with the shoulder surface 86 on the insert 68 for keeping it retained in the cavity 74, and in a substantially upright position while providing for a small amount of rotation therein as shown in FIGS. 3–6. It should be noted that the term rotation is meant to include any pivoting of the insert within the screw head 58. As can be seen, the insert 68 is not fixed with respect to the coupling member 20, instead being retained in the screw head with the staked portions 86. This allows the insert 68 to have a slight mobility, or play, and allows the insert 68 to shift independently of the screw 12 and the rod surface 28. Accordingly, the insert 68 may follow the rod surface 28 and seat itself between the rod surface 28 and the screw head 58 for a self-aligning capability.

Figure 6:
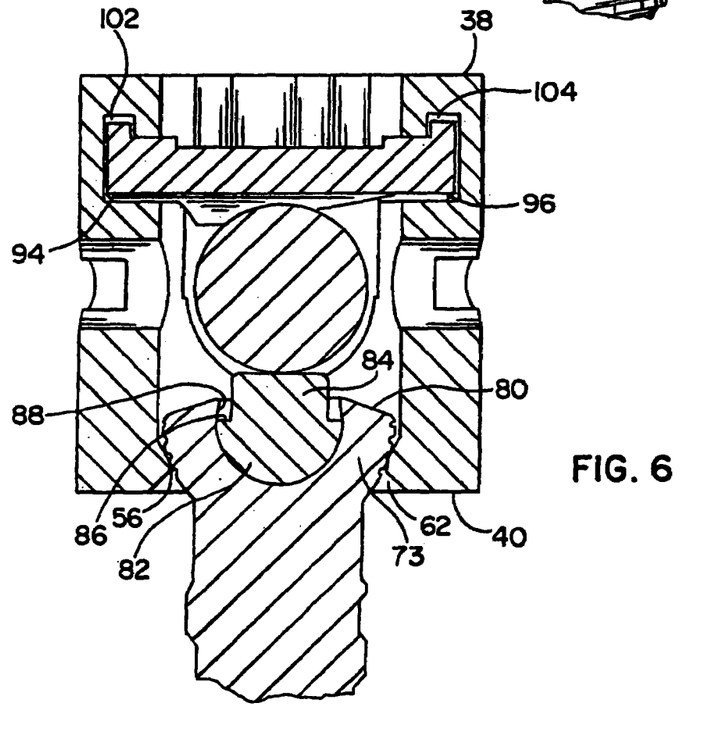
FIG. 6 is a cross-sectional view of the spinal fixation system showing the recesses formed in the coupling member configured to receive the radial flanges on the cam lock member.
Figure 7:
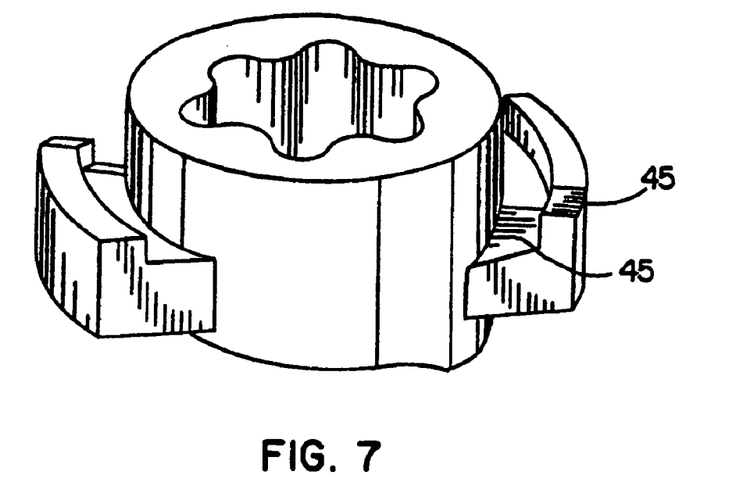
FIGS. 7–10 are various views of the cam lock member.

As previously mentioned, the cam lock member 18 does not translate along the coupling member 20 when it is turned to its locked position. In order to keep the cam lock member 18 fixed against movement in the direction along axis 21, it is provided with real flanges 90 and 92 extending radially outwardly from the annular body 30 at diametrically opposite positions thereon. The flanges 90 and 92 are received in correspondingly configured recesses 94 and 96 formed in the coupling member walls 42 and 44, as can be seen in FIG. 6. The recesses 94 and 96 have an arcuate configuration extending about axis 21 as do the radial flanges 90 and 92 for fitting therein and allowing turning of the cam lock member 18 between unlocked and locked positions thereof. The flanges 90 and 92 are received in the recesses 94 and 96 when the cam lock member 18 is turned toward its locked position. With the cam surface 34 camming on the rod surface 28, the flanges 90 and 92 in the closely conforming recesses 94 and 96 prevent the cam lock member 18 from shifting upwardly away from the spinal rod 16 and instead forces the spinal rod 16 down into clamping engagement with the insert 68 which, in turn, causes the screw head 58 and specifically outer head surface 66 to be clamped against the seat surface 54 in the coupling member 20 thus fixing the coupling device 14 relative to the bone screw 12 and anchoring the spinal rod 16 to the spinal column.

The downwardly directed clamping forces exerted by the cam lock member 18 between the screw head 58 and the bottom wall 52 of the coupling member 20 and in particular between the respective engaging surfaces 66 and 54 thereof can cause the coupling member walls 42 and 44 to spread apart. Accordingly, the flanges 90 and 92 are also provided with distal portions 90 and 100, respectively, that extend along axis 21. In this instance, the distal portions 98 and 100 are shown as being upturned from the distal ends of the radial flanges 90 and 92 although they could likewise be configured so that they extend downwardly in the direction along axis 21. The recesses 94 and 96 also include portions 102 and 104, respectively, that extend in an upward direction along the axis 21 in the coupler member walls 42 and 44 for receiving the upturned distal portions 98 and 100 on the respective radial flanges 90 and 92. With the flange portions 98 and 100 received in the recess portions 102 and 104, any spreading action of the walls 42 and 44 during the locking operation with turning of the cam lock member 18 is resisted.

As previously mentioned, the cam lock member has a contoured bottom cam surface 34 that cams on the curved cam surface 28 of the spinal rod 16. The cam surface 34 is best seen in FIGS. 8 and 10. In the illustrated and preferred form, the cam surface 34 is contoured to provide three distinct regions defined in relation to their action on the spinal rod 16. A first concave region 106 is provided to substantially mate with the rod surface 28 in the unlocked position. Concave surface region 106 extends across the bottom 34 of the cam lock member body 30 and can be aligned with the radial flanges 90 and 92. Accordingly, the radial flanges 90 and 92 will be disposed slightly above the bottom 34 of the cam lock member body 30 to accommodate the spinal rod curved surface 28 extending therebelow with the cam lock member 18 in the unlocked position thereof. In this position, the flanges 90 and 92 are not received or fully received in the recesses 94 and 96 therefor.

Diametrically opposite sections 106a and 106b of the concave surface region 106 are provided so that rotation of the cam lock member 18 in the unlocked position does not cause a camming action to occur with only a slight initial turning action thereof. With the spinal rod surface 106 aligned with the surface portions 106a and 106b, the spinal rod 16 is still loosely received under the cam lock member 18 and is not cammed thereby. Beneficially, the spinal rod 16 is captured under the cam lock member 18 so as to provide the surgeon with greater freedom of manipulation before finally locking the cam lock member 18. With continued turning of the cam lock member 18, the camming action begins at ramp regions 108 and 110 that are diametrically opposite to each other on the cap bottom surface 34 and project downwardly from the adjacent surface sections 106a, 106b along direction 21. The ramp regions 108 and 110 are configured so that the rod 16 is progressively pushed downward in the direction 21 as the cam lock member 18 is turned about the turning axis 21 toward the locked position. Accordingly, in the unlocked position these ramp surface regions 108 and 110 on the bottom cam surface 34 extend down along either side of the spinal rod 16 so as to advantageously take up the space on either side thereof thus serving to keep the space occupied by the cam lock member 18 in the coupling member 20 to a minimum for providing the overall coupling device 14 with a low profile.

Continued turning of the cam lock member 18 toward the locked position causes the rod surface 28 to be engaged against diametrically opposite generally flat surface regions 112 and 114 adjacent to the ramp surface regions 108 and 110, respectively. In an alternative form, the surface regions 112 and 114 may be a valley shape providing a depression such that the rod 12 is received into the depression. The surface regions 112 and 114 are not inclined relative to the axis 21 like the preceding ramp surfaces 108 and 110 and are the lowest point of engagement of the cam surface 34 with the rod surface 28. With the cam lock member 18 turned so that the rod surface 28 is only engaged by the surface regions 112 and 114, the cam lock member 18 is in its fully locked position with the cam lock member flanges 90 and 92 fully received in the corresponding yoke wall recesses 94 and 96 therefor, as shown in FIGS. 1 and 6. Continued turning of the cam lock member in the same direction after the fully locked position has been reached is prevented by abutment surface regions 116 and 118 adjacent to the surface regions 112 and 114, respectively. These abutment surfaces 116 and 118 extend further downwardly in direction 21 from the surface regions 112 and 114.

Accordingly, the illustrated and preferred programmed cam surface 34 provides several stages for the camming and locking action on the spinal rod 16. As shown, the cam lock member 18 can be rotated by approximately 20 degrees from the unlocked position before the rod surface 28 reaches the ramp surfaces 108 and 110. At this point, the rod 16 is cammed downwardly and the cam lock member can be turned for another 60 degrees before the rod surface 28 reaches the flat locking surfaces 112 and 114. The cam lock member 18 can then be turned by another 20 degrees before the rod surface 28 abuts against the stop surfaces 116 and 118 and the cam lock member 18 is in its fully locked position. Thus, there is approximately 100 degrees of rotation of the cam lock member 18 that is required from the fully unlocked position to the fully locked position with 20 degrees of play provided before the camming action begins and the camming of the rod 16 occurring over the final 80 degrees of rotation to the fully locked position.

Turning to more of the details, as previously mentioned, the cap cam lock member 18 includes drive surface portion 36 recessed in the top surface 32. As best seen in FIG. 2, the drive surface portion 36 can be formed with a plurality of lobes extending radially outward from the center axis 21 for receiving a similarly lobed drive tool. The lobe drive surface portions 36 provide an increased area for surface contact and torque transmission between the drive tool and the cam lock member 18.

Figure 15:
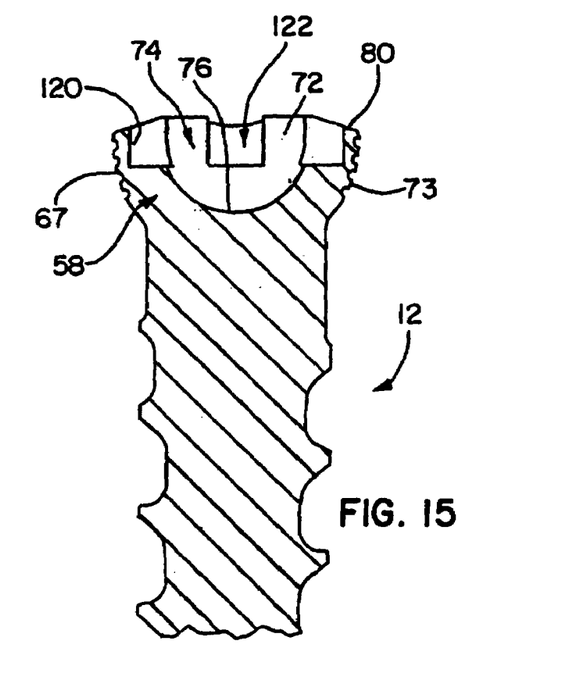

For the bone screw 12, the screw head 58 is provided with peripheral driving surfaces 120 and recessed notches 122 formed in the proximal end 78 of the screw head and recessed or notched into the top surface 80 thereof, as can be seen in FIG. 15. In this manner, a driving tool having peripheral prongs for fitting in the notches 122 can be utilized while the anvil insert 68 is in the screw head cavity 74 and slightly projecting out therefrom, as previously described.

Referring to FIGS. 1 and 11–13, it can be seen that the yoke coupler walls 42 and 44 are provided with a key slot 124 and 126, respectively, with the slots 124 and 126 having enlarged central throughbore 128 and 130 extending through the walls 42 and 44. The slots enable the coupling device 14 to be held as by arms on a device used to insert the spinal rod 16 into the coupling member 20, e.g. a rod persuader. The arms can have engaging ends that locate in the slots 124 and 126 and extend into the throughbores 128 and 130.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A spinal fixation system comprising:
a bone anchor member for being secured to a vertebral bone of the spine and having an enlarged head at one end thereof;
an elongate member for extending generally along the spine;
a coupling device for securing the elongate member relative to the bone anchor member;
a seat of the coupling device having a bore about which the seat extends sized to allow the anchor member to extend through the bore in a plurality of orientations relative to the coupling device with the head engaged against the seat; and
a one-piece cam lock member of the coupling device, the one-piece cam lock member having a cam surface thereon which, upon turning of the one-piece cam lock member about a rotary axis while the one-piece cam lock member is fixed against translation in a direction along the rotary axis, cooperates to push the elongate member downward toward the head of the bone anchor member for clamping the head of the anchor member against the seat to fix the coupling device and anchor member relative to each other with the anchor member in one of the orientations thereof and the elongate member secured between the cam lock member and the anchor member head.

2. The spinal fixation system of claim 1 wherein the coupling device includes a coupling member having an internal lower surface on which the seat is formed and an upwardly extending internal surface with the cam lock member being fixed against translation along the coupling member upwardly extending surface to keep the length thereof to a minimum.

3. The spinal fixation system of claim 1 wherein the cam lock member cams against the elongate member and the coupling device includes walls extending upward from the seat by a predetermined distance with the camming between the cam lock member and the elongate member allowing the predetermined distance to be minimized for providing a low profile for the coupling device.

4. The spinal fixation system of claim 1 wherein the cam lock member has a generally annular body and the coupling device comprises a low profile coupling member having an internal lower surface on which the seat is formed and an upwardly extending annular side surface that fits about the annular body of the cam lock member with the annular body and annular side surface being free of threading for minimizing size of the coupling member.

5. The spinal fixation system of claim 1 wherein the cam surface has a predetermined configuration so that the cam lock member is rotated by approximately 100 degrees between locked and unlocked positions thereof.

6. The spinal fixation system of claim 1 wherein the elongate member is a spinal rod having a convexly curved surface, and the cam surface of the cam lock member is a bottom surface thereof which directly engages the rod surface and includes a concave surface portion for substantially mating with the rod surface in the unlocked position, and ramp surface portions on either side of the concave surface portion that cam against the rod surface as the cam lock member is turned from an unlocked position toward a locked position thereof.

7. The spinal fixation system of claim 1 wherein the coupling device includes opposite side walls extending upwardly from the seat with the elongate member extending across the coupling device between the side walls, the cam lock member having a pair of lipped radial flanges and the side walls each including a recess configured to receive a corresponding one of the flanges therein to keep the walls from spreading apart as the cam lock member is turned for pushing the elongate member downward.

8. The spinal fixation system of claim 1 wherein the coupling device includes a generally yoke-shaped coupling member having opposite sidewalls spaced from each other and opposing slot openings therebetween through which the elongate member extends.

9. The spinal fixation system of claim 1 wherein the coupling device includes a coupling member that is configured to allow the elongate member to be secured relative to the bone anchor member, the bone anchor member head includes a recess, and
a small insert received in the recess and having a substantially flat upper surface for engaging the elongate member with the insert sized so that the upper surface is disposed only slightly beyond the anchor member head, the insert being self-adjustable in the recess to orient the upper surface to the position of the elongate member for maintaining maximum contact therebetween.

10. The spinal fixation system of claim 1 wherein the coupling device includes a saddle member having a cam surface for cooperating with the cam surface of the cam lock member and an elongate member engaging surface that is pushed tightly against the elongate member with turning of the cam lock member to a locked position thereof.

11. The spinal fixation system of claim 1 wherein the coupling device comprises a coupling member having at least one wall including a recess, and the one-piece cam lock member has at least one radial flange that is received in the recess with turning of the cam lock member to fix the cam lock member against translation in either of two opposite directions along the rotary axis of the coupling member.

12. A spinal fixation system for fixing a spinal rod in a desired position relative to a patient's spine, the spinal fixation system comprising:
a bone screw member for being secured to a vertebral bone of the spine;
a recessed head at the proximal end of the screw member having a predetermined configuration including a substantially rigid, cup-shaped wall having an upper concave recessed surface and a lower arcuate external surface;
a top surface of the rigid cup-shaped wall in which drive recesses are formed for turning the screw member into vertebral bone of the spine;
a coupling member for receiving the spinal rod and including an internal seat surface and a central bore sized to allow the screw member to extend therethrough in a plurality of different orientations with the arcuate external surface of the head bearing on the internal seat surface of the coupling member to allow the screw member head to shift thereon;
a low profile insert having a predetermined configuration including a substantially flat upper surface for engaging the spinal rod and an arcuate lower surface for adjustably bearing against the recessed surface of the screw member head with the insert in the recessed head in an unlocked position of the screw member relative to the coupling member, the insert being sized so that the upper surface thereof projects only slightly beyond the screw member proximal end to keep the profile of the insert to a minimum and the predetermined configuration and respective sizes of the screw member head and the insert providing the insert with play in the recessed head allowing the insert to shift independent of the screw member; and a clamping member that clamps the rod against the flat insert surface to fix the screw member head against the seat surface in a locked position and the screw member in one of the orientations thereof with the predetermined configuration of the screw member head staying the same in the unlocked and locked positions.

13. The spinal fixation system of claim 12 wherein the screw member head includes a retainer to keep the insert in the recess of the head.

14. The spinal fixation system of claim 13 wherein the bone screw has a threaded shank depending from the head, and the driving surfaces are for driving engagement with a tool that turns the screw with the insert in the recess thereof for threading the shank into a vertebral bone.

15. The spinal fixation system of claim 12 wherein the insert upper surface is narrower than the insert lower surface, the insert includes a shoulder between the upper and lower surfaces thereof, and staked portions of the screw member head that are in interference with the insert shoulder to retain the insert in the head recess.

16. The spinal fixation system of claim 12 wherein the insert includes an enlarged lower portion having the lower arcuate surface thereon, and a central projection extending upwardly from the lower portion and having the flat upper surface thereon.

17. The spinal fixation system of claim 12 wherein the coupling member has opposing slots sized to allow the spinal rod to extend therethrough with the insert adjusting via sliding of the insert arcuate lower surface on the upper concave surface of the screw member head to keep the insert upper flat surface in maximum contact with the rod in any one of the orientations of the screw member.

18. The spinal fixation system of claim 12 wherein the clamping member comprises a cam lock member having a cam surface thereon that cams directly against the rod with turning of the cam lock member for pushing the rod tightly against the insert.

19. A spinal fixation system comprising:

a bone anchor member;

a spinal rod having a curved external surface;

a coupling device for securing the spinal rod relative to the bone anchor member;

a cam lock member;

opposite laterally spaced openings of the coupling device through which the spinal rod extends with the bone anchor member extending transverse to the rod; and a bottom cam surface of the cam lock member that engages and cams directly against the rod curved surface as the cam lock member is turned to cause the rod to be pushed downwardly toward the bone anchor member for being fixed in position relative thereto.

20. The spinal fixation system of claim 19 wherein the bone anchor member and coupling device are distinct components.

21. The spinal fixation system of claim 20 wherein the bone anchor member includes an enlarged head and a shank depending therefrom, and the coupling device includes a coupling member having an internal lower seat surface on which the head can shift and the bore extending centrally through the seat surface sized to receive the bone anchor member shank extending therethrough in a plurality of orientations with turning of the cam lock member causing the head to be clamped against the seat to fix the shank in one of the orientations thereof.

* * * * *